(12) United States Patent
Brace et al.

(10) Patent No.: US 6,235,033 B1
(45) Date of Patent: May 22, 2001

(54) BONE FIXATION ASSEMBLY

(75) Inventors: Michael Brace, Lansdale; Hansjuerg Emch, Philadelphia, both of PA (US)

(73) Assignee: Synthes (USA), Paoli, PA (US)

( * ) Notice: Subject to any disclaimer, the term of this patent is extended or adjusted under 35 U.S.C. 154(b) by 0 days.

(21) Appl. No.: 09/453,911

(22) Filed: Apr. 19, 2000

(51) Int. Cl.$^7$ .......................... A61B 17/58; A61B 17/70; A61B 17/68
(52) U.S. Cl. ................................. 606/69; 606/60; 606/61
(58) Field of Search ................... 606/60, 61, 69

(56) References Cited

U.S. PATENT DOCUMENTS 5,470,333 * 11/1995 Ray ........................................ 606/61
6,176,861 * 1/2001 Bernstein et al. ..................... 606/61

* cited by examiner

Primary Examiner—Gene Mancene
Assistant Examiner—Michael B. Priddy
(74) Attorney, Agent, or Firm—Pennie & Edmonds LLP

(57) ABSTRACT

The present invention relates to a bone fixation assembly for securing a fixation device, such as a bone plate, to bone. The assembly includes the fixation device, a bushing, a fastening screw, and a locking screw. The bushing is seated within a through hole in the fixation device and can rotate within the through hole and has a sidewall with a bore. The sidewall has at least one slot for allowing outward expansion of the sidewall against the through hole to thereby lock the bushing at a selected angle relative to the axis of the through hole. The fastening screw has a threaded shaft for insertion through the bore of the bushing and threads into bone to secure the bushing and fixation device to bone. The head of the fastening screw fits in the bushing and includes a radial wall and open end defining a recess. The radial side wall has at least one slit for allowing outward expansion of the radial wall thereby outwardly expanding the sidewall of the bushing. The locking screw has a body that threads in the head of the fastening screw to thereby outwardly expand the radial wall of the fastening screw.

16 Claims, 4 Drawing Sheets

BONE FIXATION ASSEMBLY

CROSS-REFERENCE TO RELATED APPLICATIONS

Not Applicable

STATEMENT REGARDING FEDERALLY SPONSORED RESEARCH

Not Applicable

REFERENCE TO A MICROFICHE APPENDIX

Not Applicable

FIELD OF THE INVENTION

The present invention is directed to a bone fixation assembly, and in particular to a bushing and screw assembly for securing a fixation device to bone.

BACKGROUND OF THE INVENTION

Orthopaedic fixation devices, both internal and external, are frequently coupled to bone by the use of fasteners such as screws or pins. For example, bone plates can be secured to bone with bone screws inserted through plate holes. Securing the screws to the plate provides a fixed angle relationship between the plate and screw and reduces the incidence of loosening. One method of securing the screw to the plate involves the use of so-called "expansion-head screws." U.S. Pat. No. 4,484,570 discloses an expansion-head screw with a head that has a recess, the walls of which contain a number of slits. After the expansion-head screw is inserted into bone through a hole in the fixation device, a locking screw is inserted into the recess to expand the walls of the recess to thereby lock the screw to the fixation device.

In addition to securing the screw to the fixation device, it is also often desirable to insert the screws at an angle relative to the fixation device selected by the surgeon. The prior art discloses a number of these so-called "polyaxial" systems, most of which utilize a bushing located in a hole in the fixation device to provide for angulation of the screw relative to the fixation device. For example, U.S. Pat. No. 5,954,722 discloses a polyaxial locking plate that includes a plate hole having a bushing rotatable within the hole. As a screw is being inserted into bone through the bushing and plate hole, a threaded head of the screw engages a threaded internal surface of the bushing to expand the bushing against the wall of the plate hole, thereby locking the screw at the desired angular orientation with respect to the plate.

The present invention relates to an improved bone fixation assembly that allows for a surgeon-selected angle of a fastening screw relative to the fixation device and locking of the fastening screw once the screw is at the desired orientation.

SUMMARY OF THE INVENTION

The present invention relates to a bone fixation assembly for securing a fixation device, such as a bone plate, to bone. The assembly includes a fixation device, a bushing, a fastening screw, and a locking screw. The bushing has a sidewall with an exterior surface configured and dimensioned for polyaxial rotation within the through hole of the fixation device and an interior surface which defines a bore that extends through the upper and lower surfaces of the bushing. The sidewall has at least one slot for allowing outward expansion of the sidewall against the through hole of the fixation device to thereby lock the bushing at a selected angle relative to the axis of the through hole of the fixation device.

The fastening screw has a threaded shaft configured and dimensioned for insertion through the bore of the bushing and threadably insertable into bone to secure the bushing and fixation device to bone. The head of the fastening screw is configured and dimensioned for insertion in the bushing and includes a radial wall and open end defining a recess. The radial side wall has at least one slit for allowing outward expansion of the radial wall thereby outwardly expanding the sidewall of the bushing. The locking screw has a threaded body threadably received in the head of the fastening screw to thereby outwardly expand the radial wall of the fastening screw.

The bushing can have a substantially frustospherical shape with the bore extending through the central axis of the bushing, perpendicular to the upper and lower surfaces. In an exemplary embodiment, the bushing has an annular shoulder and the head of the fastening screw is flush with the upper surface of the bushing when the head of the fastening screw rests against the shoulder. The fastening screw can be provided with a lip protruding from the radial wall which rests on the annular shoulder when the fastening screw is threaded into the bone.

In one embodiment, the sidewall of the bushing includes a plurality of slots extending from the upper surface of the bushing. Furthermore, one of the slots can extend from the upper surface completely through the lower surface. In order to further increase the security of the bushing within the through hole, the exterior surface of the sidewall of the bushing and/or the walls of the through hole of the fixation device can be provided with ridges.

In order to eliminate the need to tap a drilled hole, the fastening screw can be a self-tapping screw. The fastening screw could also be a self-drilling screw. In an exemplary embodiment, the head of the fastening screw includes a tapered portion proximal to the threaded shaft.

In one embodiment, the recess of the fastening screw has a bottom surface with a threaded hole for threadably receiving at least a portion of the threaded body of the locking screw. The locking screw can have a tapered end. Additionally, the radial wall of the head of the fastening screw can have a matching tapered inner surface.

The present invention also relates to a method for securing a fixation device having a through hole to bone. A fastening screw is inserted through a bushing located in the through hole of a fixation device. The fastening screw is then threaded into a bone. After the threading step is completed, the fastening screw is locked to the bushing and fixation device. The fastening screw can be inserted through the bushing at a surgeon-selected orientation relative to the fixation device. The fastening screw head is preferably expanded against the bushing to thereby lock the bushing to the fixation device. A locking screw can be inserted into a recess in the fastening screw head to cause the expansion.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
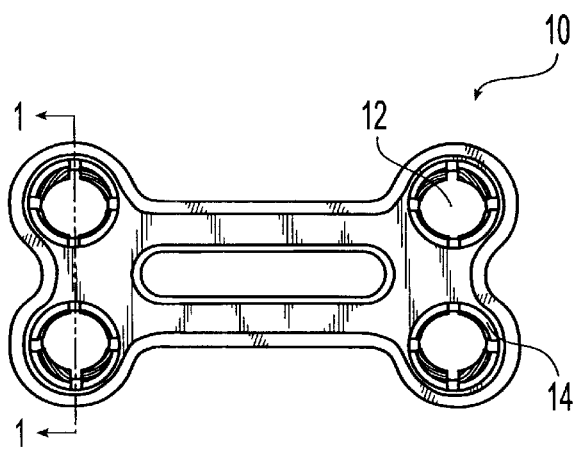
FIG. 1 shows a top view of a bone plate with four plate holes, each plate hole having a bushing according to the present invention.

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention thereto.

Figure 2:
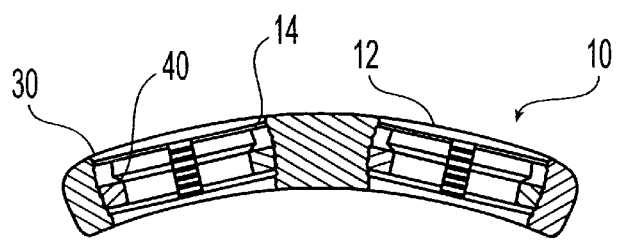
FIG. 2 shows a sectional view through line 1—1 of FIG. 1.

FIGS. 1 and 2 show a bone fixation device 10 having through holes 12 for receiving a fastener to secure device 10 to bone. Although device 10 is shown as a bone plate, device 10 can be any suitable internal or external fixation device. Examples of such devices include an external fixator, a clamp for a spinal rod, and the like. Each of through holes 12 has a bushing 14.

Figure 3:
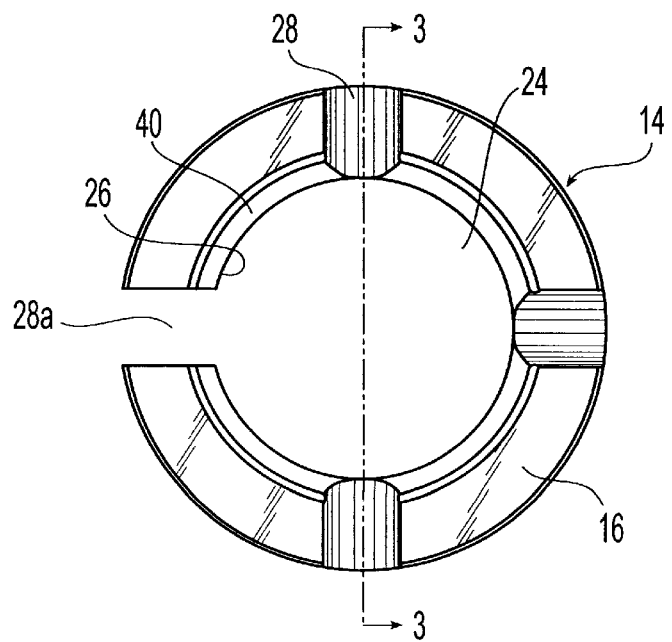
FIG. 3 shows a top view of the bushing of FIGS. 1 and 2.
Figure 4:
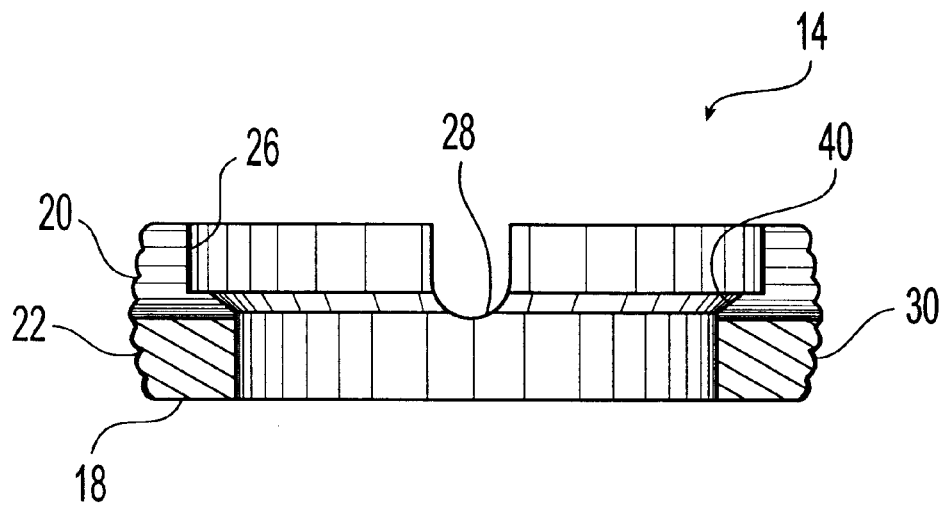
FIG. 4 shows a sectional view through line 3—3 of FIG. 3.
Figure 5:
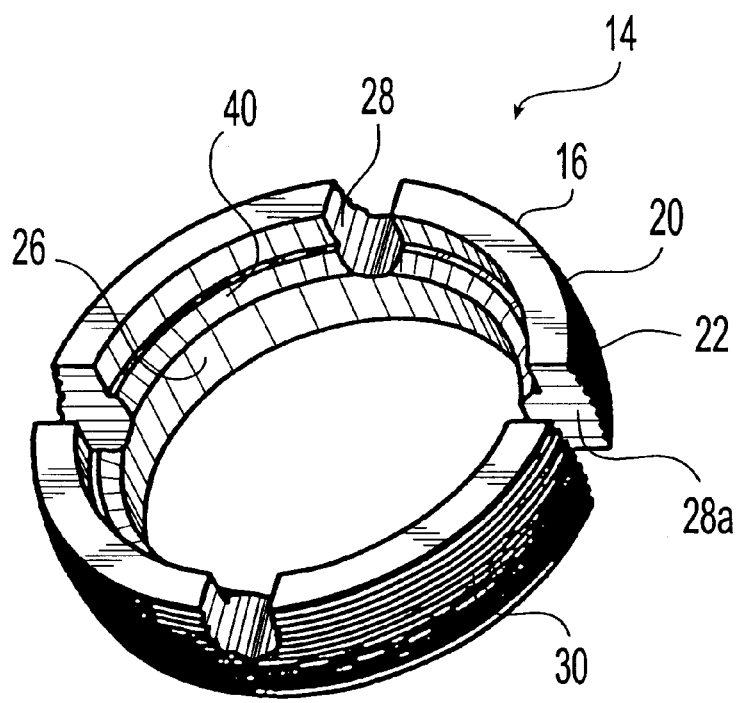
FIG. 5 shows a perspective view of the bushing of FIGS. 1–4.

As best seen in FIGS. 3–5, bushing 14 has an upper surface 16, a lower surface 18, and a sidewall 20. Sidewall 20 has an exterior surface 22 configured and dimensioned for polyaxial rotation within through hole 12. As a result and as described in more detail below, a fastener inserted through a bore 24, which is defined by an interior surface 26 of bushing 14 and extends through both upper and lower surfaces 16, 18, can be inserted at a wide variety of orientations relative to device 10. In an exemplary embodiment, bushing 14 has a frustospherical shape. Alternatively, bushing 14 can have a frustoconical shape. With either shape, bore 24 can extend through the central longitudinal axis perpendicular to the parallel upper and lower surfaces 16, 18.

Figure 9:
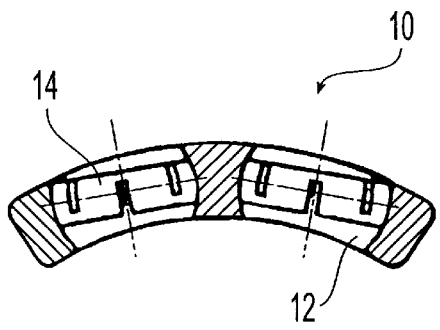
FIG. 9 shows a sectional view of a bone plate having a second embodiment of the bushing according to the present invention.

Bushing 14 includes slots 28 located on sidewall 20. Slots 28 allow sidewall 20 to expand outwardly against through hole 12. This outward expansion locks bushing 14 at the selected orientation relative to the axis of through hole 12. In order to enhance the locking effect upon expansion, exterior surface 22 of sidewall 20 and/or the periphery of through holes 12 can be provided with ridges 30. Ridges 30 provide an additional mechanism to resist motion of bushing 14 relative to device 10 once sidewall 20 has expanded outwardly. Although bushing 14 is shown having four slots, any number of slots, including one, can be used as long as the chosen number of slots provides for outward expansion of sidewall 20. As shown in FIG. 5, slot 28a extends from upper surface 16 through lower surface 18 while the rest of slots 28 do not extend through to lower surface 18. Slots 28 all extend from upper surface 16 of bushing 14. However, as shown in FIG. 9, slots 28 can extend from both upper and lower surfaces 16, 18. Although slots 28 of FIG. 9 extend in an alternating pattern, other patterns can be used.

Figure 6:
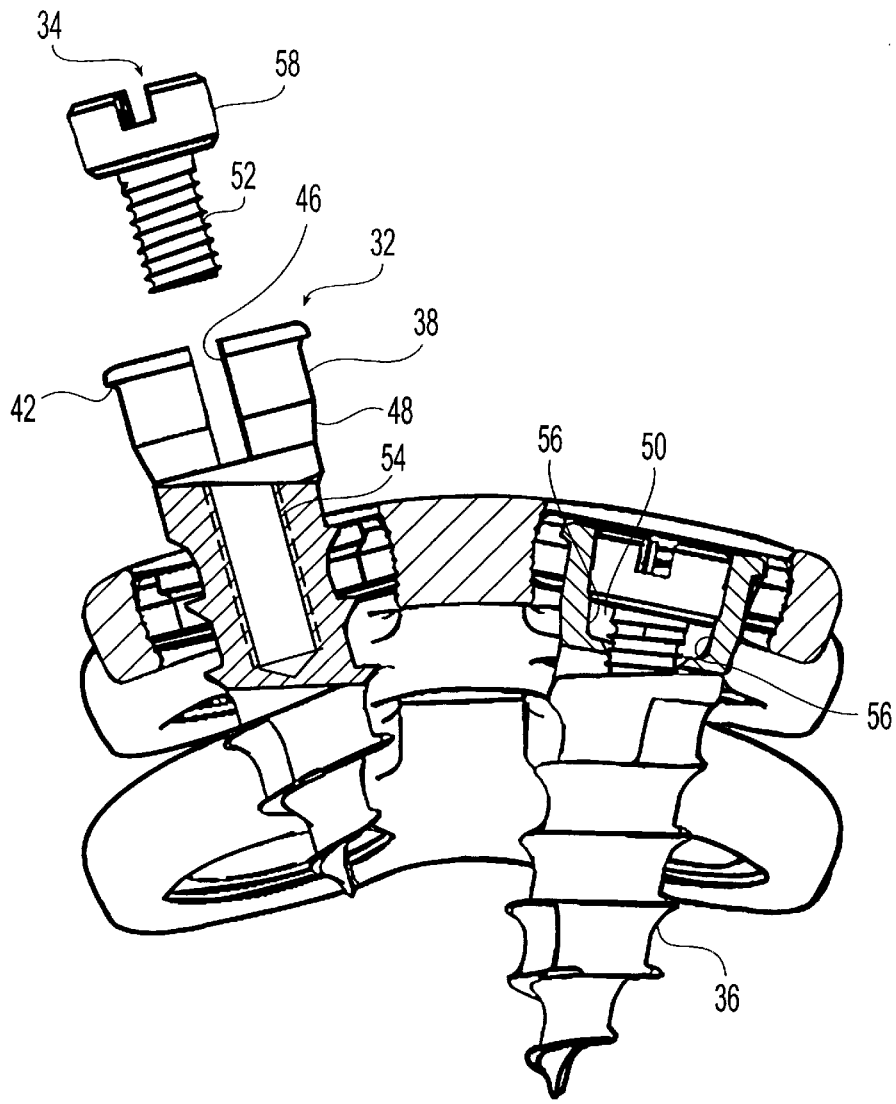
FIG. 6 shows a perspective view of a bone fixation assembly according to the present invention with a portion of the fastening screw shown in cross section to illustrate insertion of the locking screw.

As shown in FIG. 6, the bone fixation assembly according to the present invention also includes a fastening screw 32 and a locking screw 34. Fastening screw 32 has a threaded shaft 36 that inserts through bore 24 of bushing 14 and is threaded into bone to secure bushing 14 and device 10 to the bone. Fastening screw 32 can be self-tapping to eliminate the need to pre-thread the hole made in the bone. Further, fastening screw 32 can be self-drilling to also eliminate the need to pre-drill the hole. A head 38 of fastening screw 32 substantially sits within bushing 14 when fastening screw 32 has been threaded into the bone. In an exemplary embodiment, bore 24 has an annular shoulder 40 (FIG. 4) so that head 38 is flush with upper surface 16 of bushing 14 when head 38 rests against shoulder 40. This results in a low profile for the fixation assembly according to the present invention. Head 38 can be provided with a lip 42 protruding from radial wall 44. Lip 42 rests against shoulder 40 when fastening screw 32 has been threaded into the bone to further reduce the profile.

Radial wall 44 includes at least one slit 46 to enable outward expansion of radial wall 44. Thus, when head 38 is set withing bore 24 of bushing 14, outward expansion of radial wall 44 of fastening screw 32 causes outward expansion of sidewall 20 of bushing 14. Fastening screw 32 can include a tapered portion 48 proximal threaded shaft 36 to maximize the expanding effect as fastening screw 32 is threaded into bone through bore 24 of bushing 14.

As head 38 of fastening screw 32 is open-ended at its top, the open end and radial wall 44 define a recess 50 into which locking screw 34 is inserted to outwardly expand radial wall 44. Locking screw 34 has a threaded body 52 that is received in a threaded blind hole 54 in fastening screw 32. Radial wall 44 of head 38 fastening screw 32 has a tapered inner surface 56 that cooperates with tapered end 58 of locking screw 34 so that as locking screw 34 is threaded into blind hole 54, tapered end 58 urges radial wall 44 outward.

Figure 7:
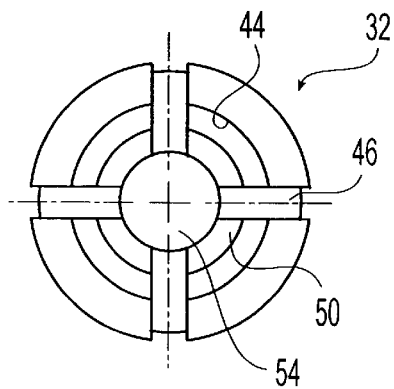
FIG. 7 shows a top view of the fastening screw of FIG. 6 prior to insertion of the locking screw.
Figure 8:
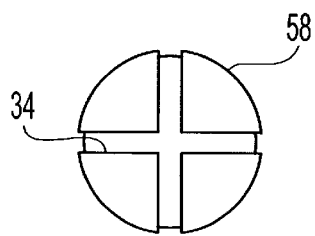
FIG. 8 shows a top view of the locking screw of FIG. 6.
Figure 10:
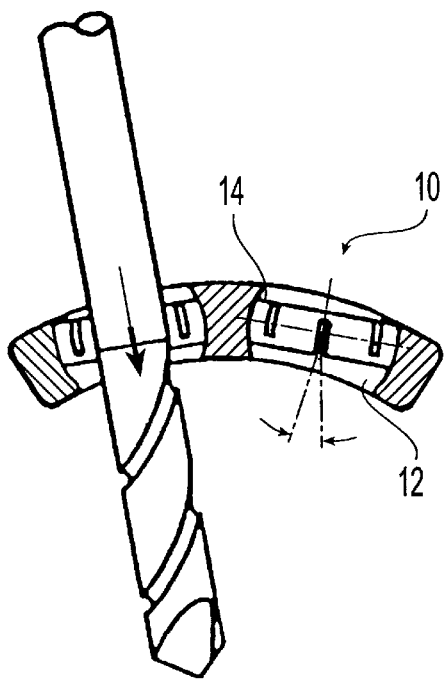
FIG. 10 shows a section view with a drill inserted in one of the plate holes.
Figure 11:
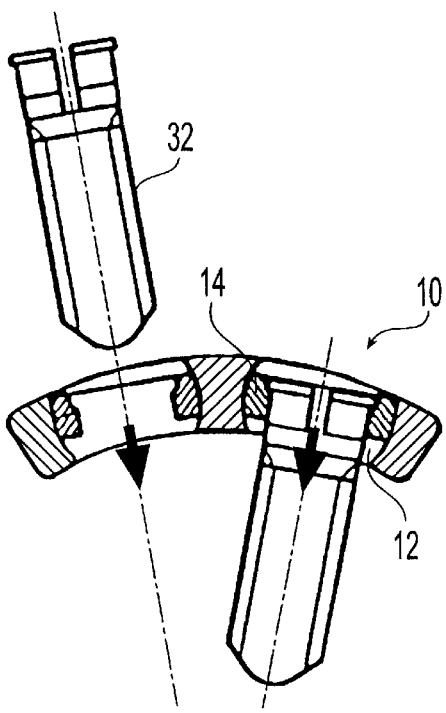
FIG. 11 shows a sectional view with the fastening screws being inserted into the bushings.
Figure 12:
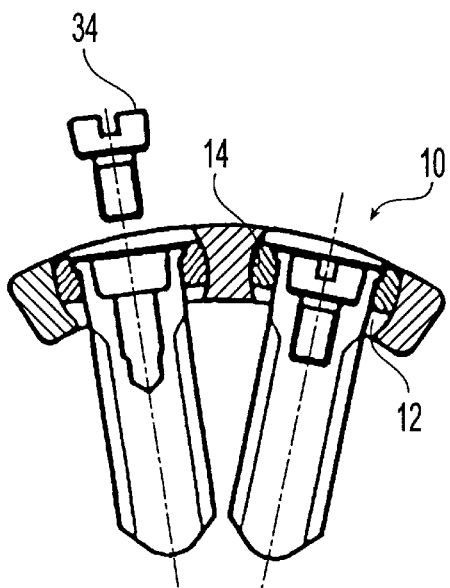
FIG. 12 shows a sectional view with the locking screws inserted into the fastening screws.

In use, bone fixation device 10 is placed against bone (FIG. 9). If fastening screw is not self-drilling, a hole is drilled through bone at the desired orientation with respect to device 10 (FIG. 10). This is achieved by rotating bushing 14 within through hole 12. Fastening screw 32 is inserted through bushing 14 and threaded into bone to secure device 10 to bone (FIG. 11). Head 38 can be provided with a mechanism for mating with a driver for threading into bone. For example, FIG. 7 shows that slots 28 are formed in a pattern that allows slots 28 to receive a blade of a driver for insertion into bone.

After fastening screw 32 is threaded into bone, locking screw 34 is then inserted into recess 50. As locking screw 34 is threaded into threaded blind hole 54, tapered end 58 of locking screw 34 pushes against radial wall 44 of fastening screw 32 to urge outward expansion of radial wall 44. This outward expansion of radial wall in turn causes outward expansion of sidewall 20 of bushing 14, thereby locking fastening screw 32, bushing 14, and device 10 to bone as a rigid construct. Because the locking of fastening screw 32 occurs after fastening screw 32 is threaded into bone, it is easier to insert fastening screw 32 into bone than some prior art designs, which result in simultaneous insertion and locking. Furthermore, because head 38 is physically deformed during the locking step (as opposed to just physical deformation of the bushing) the assembly according to the present invention improves interlocking between bushing 14 and fastening screw 32 to help ensure loosening does not occur with time.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A bone fixation assembly comprising:
   (a) a fixation device having a through hole;
   (b) a bushing having:
   (i) upper and lower surfaces;
   (ii) a sidewall with an exterior surface configured and dimensioned for polyaxial rotation within the through hole of the fixation device and an interior surface which defines a bore that extends through the upper and lower surfaces; and
   (iii) at least one slot located on the sidewall for allowing outward expansion of the sidewall against the through hole of the fixation device to thereby lock the bushing at a selected angle relative to the axis of the through hole of the fixation device;
   (c) a fastening screw having:
   (i) a threaded shaft configured and dimensioned for insertion through the bore of the bushing and threadably insertable into bone to secure the bushing and fixation device to bone;
   (ii) a head configured and dimensioned for insertion in the bushing and including a radial wall and open end defining a recess; and
   (iii) at least one slit located on the radial wall for allowing outward expansion of the radial wall thereby outwardly expanding the sidewall of the bushing; and
   (d) a locking screw having a threaded body threadably received in the head of the fastening screw to thereby outwardly expand the radial wall of the fastening screw.

2. The bone fixation assembly of claim 1 wherein the fixation device is a bone plate.

3. The bone fixation assembly of claim 1 wherein the bushing has a substantially frustospherical shape with a central longitudinal axis.

4. The bone fixation assembly of claim 3 wherein the bore extends through the central axis of the bushing and is perpendicular to the upper and lower surfaces.

5. The bone fixation assembly of claim 1 wherein the bore of the bushing has an annular shoulder and the head of the fastening screw is flush with the upper surface of the bushing when the head of the fastening screw rests against the shoulder.

6. The bone fixation assembly of claim 5 wherein the head of the fastening screw has a lip protruding from the radial wall.

7. The bone fixation assembly of claim 1 wherein the at least one slot includes a plurality of slots extending from the upper surface of the bushing.

8. The bone fixation assembly of claim 7 wherein one of the plurality of slots extends from the upper surface through the lower surface.

9. The bone fixation assembly of claim 1 wherein the exterior surface of the sidewall of the bushing includes ridges.

10. The bone fixation assembly of claim 1 wherein the through hole of the fixation device includes ridges.

11. The bone fixation assembly of claim 1 wherein the fastening screw is a self-tapping screw.

12. The bone fixation assembly of claim 1 wherein the fastening screw is a self-drilling screw.

13. The bone fixation assembly of claim 1 wherein the head of the fastening screw includes a tapered portion proximal to the threaded shaft.

14. The bone fixation assembly of claim 1 wherein the radial wall of the head of the fastening screw has a tapered inner surface.

15. The bone fixation assembly of claim 1 wherein the locking screw has a tapered end.

16. The bone fixation assembly of claim 1 wherein the recess of the fastening screw has a bottom surface having a threaded hole for threadably receiving at least a portion of the threaded body of the locking screw.

* * * * *

UNITED STATES PATENT AND TRADEMARK OFFICE
CERTIFICATE OF CORRECTION

PATENT NO. : 6,235,033 B1  
DATED : May 22, 2001  
INVENTOR(S) : Brace et al.

It is certified that error appears in the above-identified patent and that said Letters Patent is hereby corrected as shown below:

Title page,
Item [56], References Cited, U.S. PATENT DOCUMENTS, insert:

| | | | |
|---|---|---|---|
| --6,030,389 | 2/2000 | Wagner et al. | 606/71 |
| 6,022,352 | 2/2000 | Vandewalle | 606/73 |
| 6,022,350 | 2/2000 | Ganem | 606/61 |
| 6,017,345 | 1/2000 | Richelsoph | 606/70 |
| 6,001,130 | 12/1999 | Bryan et al. | 623/17 |
| 5,997,541 | 12/1999 | Schenk | 606/73 |
| 5,976,141 | 11/1999 | Haag et al. | 606/72 |
| 5,964,767 | 10/1999 | Tapia et al. | 606/73 |
| 5,961,521 | 10/1999 | Roger | 606/73 |
| 5,957,953 | 9/1999 | DiPoto et al. | 606/232 |
| 5,954,722 | 9/1999 | Bono | 606/61 |
| 5,935,169 | 8/1999 | Chan | 623/16 |
| 5,904,683 | 5/1999 | Pohndorf et al. | 606/61 |
| 5,902,303 | 5/1999 | Eckhof et al. | 606/60 |
| 5,891,145 | 4/1999 | Morrison et al. | 606/61 |
| 5,843,082 | 12/1998 | Yuan et al. | 606/61 |
| 5,807,396 | 9/1998 | Raveh | 606/69 |
| 5,800,433 | 9/1998 | Benzel et al. | 606/61 |
| 5,797,912 | 8/1998 | Runciman et al. | 606/69 |
| 5,797,911 | 8/1998 | Sherman et al. | 606/61 |
| 5,735,853 | 4/1998 | Olerud | 606/71 |
| 5,713,900 | 2/1998 | Benzel et al. | 606/61 |
| 5,681,312 | 10/1997 | Yuan et al. | 606/61 |
| 5,681,311 | 10/1997 | Foley et al. | 606/61 |
| 5,676,667 | 10/1997 | Hausman | 606/69 |
| 5,676,666 | 10/1997 | Oxland et al. | 606/61 |
| 5,616,144 | 4/1997 | Yapp et al. | 606/61 |
| 5,607,428 | 3/1997 | Lin | 606/69 |
| 5,571,184 | 11/1996 | DeSatnick | 623/13 |
| 5,549,612 | 8/1996 | Yapp et al. | 606/69 |
| 5,520,690 | 5/1996 | Errico et al. | 606/61 |
| 5,501,684 | 3/1996 | Schlapfer et al. | 606/73 |
| 5,486,176 | 1/1996 | Hildebrand et al. | 606/71 |
| 5,474,553 | 12/1995 | Baumgart | 606/71 |
| 5,269,784 | 12/1993 | Mast | 606/69 |
| 5,261,910 | 11/1993 | Warden et al. | 606/61 |
| 5,151,103 | 9/1992 | Tepic et al. | 606/69 |
| 5,127,914 | 7/1992 | Calderale et al. | 606/65 |
| 5,057,111 | 10/1991 | Park | 606/69 |
| 5,053,036 | 10/1991 | Perren et al. | 606/69 |
| 5,041,113 | 8/1991 | Biedermann et al. | 606/61 |
| 5,013,313 | 5/1991 | Surer | 606/60 |
| 4,836,196 | 6/1989 | Park et al. | 128/92 YM |
| 4,484,570 | 11/1984 | Sutter et al. | 128/92 D |
| 4,388,921 | 6/1983 | Sutter et al. | 128/92B |
| 3,596,656 | 8/1971 | Kaute | 128/92  --. |

UNITED STATES PATENT AND TRADEMARK OFFICE
CERTIFICATE OF CORRECTION

PATENT NO.   : 6,235,033 B1
DATED         : May 22, 2001
INVENTOR(S)  : Brace et al.

It is certified that error appears in the above-identified patent and that said Letters Patent is hereby corrected as shown below:

<u>Title page cont'd,</u>
Item [56], References Cited, FOREIGN PATENT DOCUMENTS, insert:
-- WO   WO  88/0378   6/1988 --.

Signed and Sealed this

Twenty-second Day of July, 2003

JAMES E. ROGAN
*Director of the United States Patent and Trademark Office*